United States Patent [19]
Alul et al.

[11] Patent Number: 5,166,407
[45] Date of Patent: Nov. 24, 1992

[54] PROCESS FOR PREPARING FATTY PEROXYACID PRECURSORS HAVING AMIDE MOIETIES IN THE FATTY CHAIN

[75] Inventors: Husni R. Alul, St. Louis; Dario R. Cova, Kirkwood, both of Mo.

[73] Assignee: Monsanto Company, St. Louis, Mo.

[21] Appl. No.: 826,555

[22] Filed: Jan. 27, 1992

[51] Int. Cl.$^5$ .................................. C07C 229/00
[52] U.S. Cl. .................................. 560/155
[58] Field of Search .......................... 560/155

[56] References Cited

U.S. PATENT DOCUMENTS

| | | | |
|---|---|---|---|
| 2,604,449 | 7/1952 | Bryant | 560/155 |
| 2,728,487 | 2/1953 | Drake | 560/155 |
| 2,742,432 | 4/1956 | Messina | 560/155 |
| 3,214,460 | 10/1965 | McGee | 560/155 |
| 3,296,303 | 1/1967 | Nemec et al. | 260/558 |
| 3,324,179 | 6/1967 | Scholz et al. | 260/561 |
| 3,417,114 | 12/1968 | Kuceski | 260/404 |
| 3,816,510 | 6/1974 | Massie | 560/155 |
| 4,588,833 | 5/1986 | Kadelka | 560/155 |
| 4,634,551 | 1/1987 | Burns | |
| 4,659,866 | 4/1987 | Batt et al. | 564/137 |
| 4,981,987 | 1/1991 | Sugimori et al. | 556/419 |

FOREIGN PATENT DOCUMENTS

| | | |
|---|---|---|
| 631367 | 11/1949 | United Kingdom . |
| 1108395 | 4/1968 | United Kingdom . |

*Primary Examiner*—Michael L. Shippen
*Attorney, Agent, or Firm*—R. C. Loyer

[57] ABSTRACT

A process for preparing precursors for amido containing organic peracids is disclosed wherein a diester of a dibasic acid is reacted with an amine to provide a mono amido ester carboxylic acid ester. The reaction is conducted in the presence of a catalytic amount of a carboxylic acid whereby the rate of reaction to form the mono amido ester of the dibasic acid is increased. The esters are converted to acids highly desirable as precursers for peracids useful as bleaches in laundry detergents.

17 Claims, No Drawings

PROCESS FOR PREPARING FATTY PEROXYACID PRECURSORS HAVING AMIDE MOIETIES IN THE FATTY CHAIN

This invention relates to the preparation of fatty acids which are to be oxidized to provide bleaching compounds comprising fatty peroxyacids and salts thereof.

BACKGROUND OF THE INVENTION

The discovery of highly stable organic peracid molecules is critical to the commercialization of detergent formulations containing peracid bleaches. Such peracids have recently been discovered which are highly crystalline and have relatively high melting points. Also, it is highly important for highly stable bleaches to be prepared in a manner which eliminates, or at least minimizes contamination from metals. Metals or metal ions are particularly deleterious to peracids because they catalyze the decomposition of the peroxygen group.

Consequently, the detergent industry requires peracids which are highly stable, have high melting points and are conveniently manufactured in high volume. Because of their high melting points both the peracids and their precursors are typically purified by precipitation or crystallization techniques. Metal ions typically present in the crystallization media become trapped in the peracid crystals and become impurities which reduce the stability of the peracid. The amount of metal ion contamination is directly related to stability of the peracid.

A recent patent, U.S. Pat. No. 4,634,551 to Burns et al describes novel, relatively stable and high melting crystalline amide peracids. Generally, the precursors to these amide peracids, that is, the amido acids, were reported to have been prepared by the reaction of the appropriate acid chloride with the appropriate amine followed by precipitation of the resulting amido acid.

The peroxyacids found in U.S. Pat. No. 4,634,551 are represented by the formula

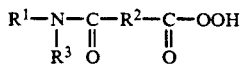

where in $R^1$ is selected from the groups consisting of alkyl, aryl or alkaryl radicals containing from about 1 to about 14 carbon atoms, $R^2$ is an alkylene group containing from 2 to 14 carbon atoms and $R^3$ is H or an alkyl, aryl or alkaryl group containing from 1 to about 10 carbon atoms, the total number of carbon atoms being from about 10 to about 20.

It has been found that the most efficient way to prepare the amide peracids is to first prepare the diester of a dibasic acid and then react the diester with an amine to provide a mono amido ester which can then be converted to the amide peracid. Such a process provides high yields of high quality product. This process also avoids acid chlorides which are relatively expensive and increases the burden of waste disposal. However, most processes for the production of the mono amido ester from the reaction of a diester with an amine produces a mixture of compounds and most prominently an undesired amount of the very stable diamide which has no economically attractive utility.

The reaction of an alkyl amine with, for example, the diester of adipic acid is well known as in U.S. Pat. No. 3,417,114 to Kueski. It is noted therein that esters of mono-, di, tri, or tetracarboxlyic acids may be employed wherein the resulting amide may contain one or more ester groups, depending on the extent to which the ester groups are converted to amide groups. However, no indication is given as to how to provide a selective reaction to produce a mono amido ester of a dibasic acid.

The production of amides by reaction in a column is described in U.S. Pat. No. 3,324,179 to Scholz et al. This patent discloses the reaction of four carbon fatty acids with alkylamines wherein the amine reactant is in excess or at least in stoichiometric amounts. Reflux ratios in the range of 2:1 to 30:1 are disclosed.

The production of methyl formamide by the reaction of ammonia and methyl formate in a reaction column is disclosed in U.S. Pat. No. 4,659,866 to Kaspar et al. It is reported that virtually quantitative conversion to the amide is provided in a continuous process. However, this process involves the conversion of a monoester to a monoamide.

Diamides are prepared in high purity according to U.S. Pat. No. 3,296,303 to Nemec et al by the reaction of a secondary amine with a diacid or diester wherein the diester is derived from selected ethylene or propylene glycols. The amidation step is conducted by employing the amine in a ratio with the ester or acid of at least 2:1. The process seeks to avoid the production of a mixture containing monoester amides.

Amides are also produced in the presence of water at relatively low temperatures by employing catalysts according to U.K. 1,108,395. There is reference to conducting such reactions in a column. Amides are prepared at temperatures of less than 30° C. with catalysts, consisting of ion exchange resins, either strongly basic or strongly acid.

The reaction of esters with amines to provide amides is also disclosed in U.K. 631,367 to Meade which teaches the use of a basic catalyst consisting of an alkali metal alcoholoxide.

Although considerable work has been done in the art of preparing amides, the provision of a selective reaction of an amine with a dibasic acid to provide a high proportion of mono amido ester of such dibasic acid has not heretofore been discovered. In the production of large quantities of such material it is vital to reduce the amount of unwanted production of diamides to provide an environmentally sound, mass production process yet provide reasonably rapid reaction rates to provide the mono amido ester.

Attempts to provide the mono amido ester of dicarboxylic acids has resulted in a relatively low yield of the desired product. The above mentioned patent to Kuceski indicates recovery from a catalyzed reaction of about 40% by weight of the mono amido ester of adipic acid, based upon the weight of the original starting material.

It is therefor desirable to have a process for producing mono amido esters of dibasic acids which proceeds quickly and selectively so as to minimize the production of the diamide.

BRIEF DESCRIPTION OF THE INVENTION

In accordance with this invention there is provided a process for preparing precursors of fatty peroxyacids or salts thereof having amide moieties in the fatty chain.

More specifically, in accordance with this invention there is provided a process for preparing a mono amido ester of a dicarboxylic acid which comprises esterifying a polycarboxylic acid of the formula

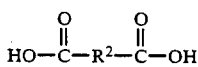

with a lower alkyl alcohol followed by reacting the ester with a monoalkylamine of the formula

wherein R is an alkyl radical having from 1 to 20 carbon atoms and $R^2$ is as defined above in the presence of a catalytic amount of an ammonium salt forming acid which dissociates to reform the amine and acid at the reaction temperature of the ester and amine whereby the rate of reaction to form the mono amido ester is increased.

It has been found that by including up to about 1%, by weight of the diester, of a weak acid catalyst of this invention the reaction rate to provide the mono amido ester is increased 10 to 40 times that observed without a catalyst. The preferred catalyst for preparing the mono amido ester of a dibasic acid is the mono ester of such an acid. Thus, for example, a preferred catalyst for the reaction of the diester of adipic acid with an amine is the monoester of adipic acid.

DETAILED DESCRIPTION OF THE INVENTION

Typical dibasic acids include those having from 2 to 14 carbon atoms between the carboxyl groups. Preferably the dibasic acids useful in this invention contain from about 2 to about 10 carbon atoms between the carboxyl groups and are aliphatic, straight chained. Included are adipic acid, glutaric acid, succinic acid, pimelic acid, suberic acid, azelaic acid, sebacic acid, and dodecanedioic acid.

Any number of alcohols may be employed to provide the diester. However, since the final product is a mono amido ester which is separated from a reaction mixture containing small amounts of unreacted diester, the alcohol is chosen so as to provide easily distinguishable properties as between the diester and mono amido ester. Accordingly any suitable ester forming alcohol may be employed. Examples of such alcohols are methanol, ethanol, propanol, isopropanol, n-butanol, hexanol, octanol, and other low molecular weight alkyl alcohols. Alkyl alcohols containing from about 1 to 4 carbon atoms are preferred and normal alcohols are preferred when higher molecular weight alcohols are employed. Methanol is preferred when the dibasic acid is adipic acid.

The catalyst employed in the esterification step is preferably toluene sulfonic acid. However, other inorganic acid catalysts may be employed. Such catalysts include phosphoric acid, sulfuric acid, methane sulfonic acid, etc. The use of such catalyst allows esterification at lower temperatures than uncatalyzed esterification. It has also been found that the esterification proceeds with greater efficiency at lower temperature, such as 80° C. than uncatalyzed at 100° C. Also, the esterification proceeds with greater completion and selectivity in the presence of a catalyst. A large number of acids are known to be useful as a catalyst and may be selected as the esterification catalyst. Other suitable inorganic acids include hydrochloric acid and phosphoric acid. Only a small amount of catalyst is required and the amount varies depending upon the dibasic acid employed. Usually the amount of catalyst employed is in the range of from 0.1% to about 1%, by weight of the dibasic acid. The catalyst enables the esterification reaction to proceed at a much lower temperature than otherwise possible.

It is usual that the dibasic acid is soluble in the alcohol and therefore the alcohol is employed as a diluent as well as a reactant. Also, it is desirable to remove water from the reactor both before and during the reaction. Constant removal is required because water is formed during esterification continuously. Removal is conveniently achieved by purging with alcohol at a temperature in excess of the boiling point of the reaction mixture. A mixture of water and alcohol is taken off overhead. When methanol is employed the reaction mixture is held at a temperature in the range of from about 95° C. to about 125° C. For this reason, about a three-fold excess of methanol is employed. Recovery of the alcohol by means such as distillation provides dry alcohol for reuse. The diester is recovered from the reaction mixture by any convenient means such as by vacuum distillation.

The reaction is economical in that the yield of diester is very high, (>95% in the case of dimethyl adipate) and the residue may be recycled.

In the process of this invention the diester is reacted with an amine to provide a distillable mono amido ester. The alcohol formed is removed and recycled. The reaction is monitored by GC analysis or by titration of the reaction mixture for residual amine. It is usual that the reaction providing the amide takes place almost instantaneously at higher temperatures and in about 1 to about 5 hours at a temperature in the range of from about 70° C. to about 200° C. Usually the reaction between the amine and the ester is carried out with an excess of ester to maximize production of the desired mono amido ester and to minimize formations of diamide by-product. Such excess is surprisingly large to provide the mono amido ester. Excess as high as 20 to 1 on a mole basis may be employed. In most instances the excess of diester over amine is in the range of from about 3 to 10 moles of diester per mole of amine. The mole ratio is preferably about 5 to 10 moles of diester to 1 mole of amine.

Amines employed in the process of this inventions are primary amines containing either straight or branched chain alkyl groups. Typically the amine contains from 1 to 20 carbon atoms and preferably from about 6 to about 12 carbon atoms. Such preferred amines are commercially available. Typical amines include hexylamine, heptylamine, octylamine, nonylamine, decylamine, dodecyclamine and undecyl amine. The linear or straight chain alkyl amines are preferred because the final amido acid has higher melting points than branched chained amido acids.

Any number of weak organic acids can be employed as a catalyst in the process of this invention. As noted above, the preferred catalyst is the mono ester of the dibasic acid which is being reacted with an amine in the diester form. That is, the mono ester of the above mentioned dibasic acids may be employed. Also, other weak organic acids may be employed such as acetic, adipic, propionic, butyric oxalic, citric, decanedioic, dodecanedioic and the like. The requirement of the acid is that it is not strong enough to provide a stable ammonium salt at the reaction temperature of the diester and amine. To be a suitable catalyst in accordance with this invention the ammonium salt formed upon addition of the organic acid must dissociate upon heating to the amidation reaction temperature yielding the free acid and free amine. If the acid is too strong the required dissociation does not occur and no increase in reaction is observed. For example, toluene sulfonic acid has failed to provide a catalytic effect as indicated by the reaction rate when added as described herein. Toluene sulfonic acid formed a salt which was stable at the reaction temperature of the diester and amine to form the mono amido ester of the dibasic acid. While any amount of such acid in the reaction mixture is beneficial to increase the mono amidation reaction rate, it has been found that an amount in excess of about 1%, by weight based on the diester, does not further increase the reaction rate. Preferably the amount of catalyst is in the range of from about 0.2% to about 1% by weight of the diester.

To provide high purity mono amido ester the reaction mixture may be subjected to a two-step distillation procedure. The unreacted diester and traces of amine are first removed by distillation at relatively low temperature. Thereafter, the desired mono amido ester is distilled at high temperature under reduced pressure. It has been found that high vacuum enables the efficient separation of the desired product from undesired impurities, particularly metals. The term "reduced pressure" in this specification and claims means pressure within the distillation column of no more than about 10 mm Hg. Such reduced pressure is maintained during recovery of the desired mono amido ester. The temperature of the distillation depends upon the dibasic acid and the amido group. Usually, the temperature employed to distill the mono amido ester is in the range of from about 100° C. to about 300° C. but this depends upon the specific material being recovered. The diamide by-product has been found to be usually a much higher boiling material than the mono amido ester thereby allowing efficient separation by distillation.

Further, the process of this invention may be carried out in a reaction column wherein it is possible to remove the alcohol produced in the reaction overhead and to remove the product mono amido ester from the bottom. In such manner the process is most advantageously carried out in a continuous manner by feeding the reactants, diester and amine, at different points in the column. When employing a reaction column in the process of this invention the amount of molar excess diester over the amine may be greatly reduced below the above-mentioned ratios.

DESCRIPTION OF THE PREFERRED EMBODIMENTS PREPARATION OF NONYLAMIDO METHYL ADIPATE

EXAMPLE 1
PRIOR ART

Into a reactor fitted with an agitator, a distillation column, heating mantle and feed tube there was placed 229 g of dimethyl adipate and 14.6 g of nonyl amine. The contents of the reactor were heated to a temperature of 140° C. Samples of the reaction mixture were taken every 5 minutes to determine the reaction rate by analysis of the sample. In Table I below there is shown the analytical results obtained. In Table I NA stands for nonyl amine, DMA stands for dimethyl adipate and NAMA stands for nonyl amido methyl adipate. The analytical results are stated in weight percent of the reaction mixture. Small amounts of by-product are not accounted for in the data presented below.

TABLE 1

| Sample | Time (Min.) | NA | DMA | NAMA |
|---|---|---|---|---|
| 1. | 5 | 6.68 | 92.79 | 0.45 |
| 2. | 10 | 6.42 | 92.89 | 0.61 |
| 3. | 15 | 6.38 | 92.72 | 0.81 |
| 4. | 20 | 6.24 | 92.60 | 1.08 |
| 5. | 25 | 6.00 | 92.50 | 1.42 |
| 6. | 30 | 5.83 | 92.30 | 1.79 |

EXAMPLE 2

The above described reaction was repeated with the exception that mono methyl adipate ester was added to the reaction mixture in an amount of 0.85%, by weight of the dimethyl adipate. Samples of the reaction mixture were taken at 5 minute intervals and the analysis reported in Table II below wherein the abbreviations have the same meaning and the analysis is reported on the same basis as in Example 1. As in Example 1, small amounts of by-product are not accounted for in the data below.

TABLE II

| Sample | Time (MIN) | NA | DMA | NAMA |
|---|---|---|---|---|
| 1 | 5 | 2.9 | 91.5 | 5.4 |
| 2 | 10 | 1.7 | 89.8 | 8.2 |
| 3 | 20 | 0.6 | 88.3 | 10.8 |
| 4 | 25 | 0.3 | 88.6 | 10.8 |
| 5 | 30 | 0.2 | 88.2 | 11.3 |

What is claimed is:

1. A process for the preparation of a mono amido ester of a dibasic acid represented by the formula $$R-\underset{\underset{H}{|}}{N}-CR^2-\underset{\underset{}{}}{\overset{O}{\overset{\|}{C}}}-\overset{O}{\overset{\|}{C}}OX$$

wherein R is an alkyl group having from 1 to 20 carbon atoms, $R^2$ is an alkylene group containing from 2 to 14 carbon atoms and X is an alkyl radical having from 1 to 8 carbon atoms which comprises reacting the diester of said dibasic acid with monoalkyl amine of the formula $RNH_2$ wherein R has the same meaning as above at a temperature in the range of from about 70° C. to about 200° C. in the presence of a catalytic amount of a carboxylic acid whereby the rate of reaction to form the mono amido ester is increased.

2. The process of claim 1 wherein the amine is n-nonylamine.

3. The process of claim 2 wherein the ester of the dibasic acid is dimethyl.

4. The process of claim 3 wherein the dibasic acid is adipic acid.

5. The process of claim 1 wherein the catalyst is the mono ester of the dibasic acid.

6. The process of claim 5 wherein the catalyst is present in an amount of up to about 1%, by weight of said diester.

7. The process of claim 5 wherein the catalyst is a mono ester of adipic acid.

8. The process of claim 7 wherein the mono ester is monomethyl adipate.

9. The process of claim 1 wherein the catalyst is selected from the group consisting of the mono ester of said dibasic acid, acetic acid, adipic acid, butyric acid, oxalic acid, citric acid, decanedioic acid and dodecanedioic acid.

10. The process of claim 7 wherein the mono amido ester is removed from the reaction mixture by distillation under reduced pressure.

11. The process of claim 1 wherein the reaction is conducted in a reaction column 12. The process of claim 12 wherein the reaction is continuous by removing the alcohol produced in the reaction overhead and removing the mono amido ester from the bottom.

13. The process of claim 1 wherein the dibasic acid is selected from the group consisting of succinic, glutaric, adipic, suberic and azelaic acids.

14. The process of claim 4 wherein the mole ratio of dimethyl adipate to n-nonylamine is in the range of from about 20 to 1 to about 1 to 1.

15. The process of claim 14 wherein the mole ratio is in the range of from about 10 to 1 about 3 to 1.

16. The process of claim 14 wherein the mole ratio is in the range of from about 10 to 1 to about 5 to 1.

17. The process of claim 1 wherein the amine contains from 6 to 12 carbon atoms.

* * * * *